United States Patent [19]

Pasternak

[11] Patent Number: 4,608,376
[45] Date of Patent: Aug. 26, 1986

[54] OPIATE AGONISTS AND ANTAGONISTS

[75] Inventor: Gavril W. Pasternak, New York, N.Y.

[73] Assignee: Carolyn McGinnis, New York, N.Y.

[21] Appl. No.: 430,630

[22] Filed: Sep. 30, 1982

Related U.S. Application Data

[63] Continuation-in-part of Ser. No. 312,018, Oct. 16, 1981, abandoned.

[51] Int. Cl.$^4$ .................. C07D 491/22; C07D 471/18; A61K 31/485
[52] U.S. Cl. ..................................... 514/282; 514/286; 546/45; 546/74
[58] Field of Search .................... 546/45, 74; 514/282, 514/286

[56] References Cited

U.S. PATENT DOCUMENTS 2,797,221 6/1957 Gates ...................................... 546/45
4,362,870 12/1982 Portoghese ........................ 542/403

OTHER PUBLICATIONS

Pasternak, Science, 208 514(1980).
Noller, "Chemistry of Organic Compounds", 3rd Edition, 1965, p. 286, 234.
Smith, "The Chemistry of Open Chain Nitrogen Compounds" vol. 2, pp. 181-182.
Freund et al., Chem. Berichte, 53, pp. 2250-2253, 2260-2261, (1920).
Speyer et al., Chem. Berichte, 57, pp. 1422-1427, (1924).
Sargent et al., Chemical Abstracts, vol. 53, 14133a-14134c, (1959).
Bentley, Chemistry of the Morphine Alkaloids, Clarendon Press, Oxford, (1954), pp. 259, 262.
Sawa et al., Tetrahedron, vol. 24, pp. 6185-6196, (1968).
Pasternak et al., J. Med. Chem., 23(6), pp. 674-676, (1980).
Hahn et al., Life Sci., 31(12-13), pp. 1385-1388, (1982).
Hahn et al., J. Neurosci., 2(5), pp. 572-576, (1982).

Primary Examiner—Mark L. Berch
Attorney, Agent, or Firm—Felfe & Lynch

[57] ABSTRACT

Dihydromorphinone compound of the general formula

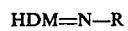

wherein
HDM is

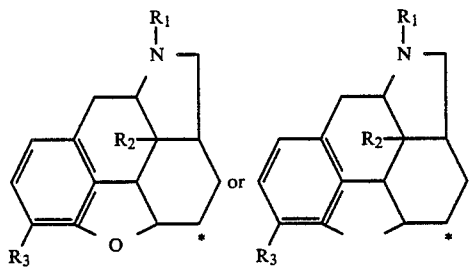

where
* indicates binding carbon
R1 is an optionally substituted alkyl, alkylene, cycloalkyl, or cycloalkylene
R2 is OH or H
R3 is OH or OCH3 and
R is N=R4, N—R4,

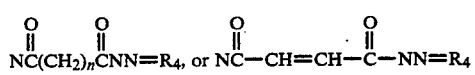

R4 is an optionally substituted alkyl, alkylene, cycloalkyl, cycloalkylene, aryl, heterocycloalkyl, heterocycloalkylene, or alkenyl, and
n is 1-10, and use thereof as an opiate receptor blocker.

3 Claims, 3 Drawing Figures

OPIATE AGONISTS AND ANTAGONISTS

The invention described herein was made in the course of work under a grant or award from the Department of Health, Education and Welfare.

CROSS REFERENCE TO RELATED APPLICATION

This application is a continuation-in-part of U.S. application Ser. No. 312,018 filed Oct. 16, 1981 (now abandoned).

BACKGROUND

The advantages of irreversible drugs in both the in vivo and in vitro evaluation of opiate action has led to the recent development of a number of irreversible opiate agonists and antagonists (Caruso et al. Science 204:316–318, 1979; Portoghese et al, J. Med. Chem. 22:168–173, 1978; Portoghese et al, J. Med. Chem 22:168–173, 1979; Schultz and Goldstein, Life Sc. 16:1843–1848, 1975; Winter and Goldstein, Mol ec Pharmacol 8:601–611, 1972). One compound, naloxazone, has been particularly useful in characterizing opiate receptors and opiate actions because of its ability to selectively inhibit the high affinity, or $mu_1$, binding sites as well as blocking opiate analgesia with little effect on other classes of binding sites or opiate-induced lethality (Pasternak et al Science 208:514–516, 1980; J. Pharmacol Exp. Therap 214:455–462, 1980; Zhang and Pasternak, Life Sc. 29:843–851, 1981; Pasternak, in press). However, naloxazone requires high doses both in vivo and in vitro to inactivate these high affinity, or $mu_1$, binding sites and the mechanism of its activity was unrecognized, (mu site classification is described in-Wolozin and Pasternak, Proc. Natl. Acad. Sci., Vol. 78, pg. 6181–6185 (1981).

IN THE DRAWINGS

Rat brain membranes were prepared and incubated with naloxone ( $\circ$ ) or naloxonazine ( $\bullet$ ) at the stated concentration for 30 min at 25° C. and then washed four times and finally assayed with [$^3$H] dihydromorphine (1.2 nM). Results are from a single experiment which has been replicated three times.

Figure 3:
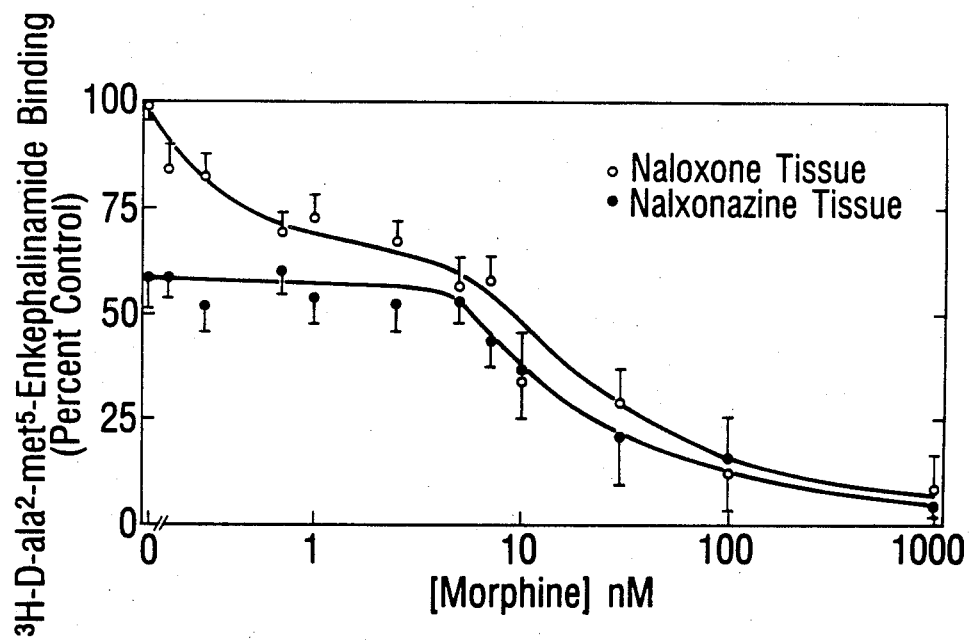

FIG. 3 shows morphine displacement of [$^3$H] D-ala$^2$-met$^5$-enkephalinamide binding in naloxone and naloxonazine treated tissue.

Rat brain membranes were prepared and incubated with either naloxone (50 nM; $\circ$) or naloxonazine (50 nM; $\bullet$) for 30 min at 25° C. and washed three times. Binding of [$^3$H]D-ala$^2$-met$^5$-enkephalinamide (1.5 nM) was then measured in the absence and presence of various concentrations of morphine sulfate. Values are expressed as percent of binding in the naloxone treated tissue in the absence of morphine and represent a single experiment which has been replicated three times.

DESCRIPTION

This invention relates to the 14-hydroxydihydromorphinone hydrazones (naloxazone, oxymorphazone and naltrexazone) and their irreversible binding to opiate receptors probably by the formation of their azines. These azines, naloxonazine, naltrexonazine and oxymorphinazine, irreversibly block opiate binding in vitro 20–40 fold more potently than their corresponding hydrazones, naloxazone, naltrexazone and oxymorphazone. The blockade of binding by naloxonazine shows the same selectivity for high affinity, or $mu_1$, sites as naloxazone.

Naloxazone proved very useful in our understanding of opiate receptor subtypes and their correlation with analgesia (Pasternak et al, 1980 supra; Pasternak and Hahn, J. Med. Chem. 23:674–677, 1980; Zhang and Pasternak, Life Sci 29:843–851, 1981; Hazum et al, Life Sci. 28:2973–2979; 1981; Pasternak, Proc. Nat. Acad. Sci. USA 77:3691–3694, 1980; Pasternak et al in press), even though its mechanism of action was not known. The high concentrations and doses required for irreversible activity led us to the conclusion that a more active component was being formed. This active component is believed to be azine, one of the inventive compounds.

Although previously unrecognized, it has now been found that although the naloxazone used was chemically pure, a small amount rearranged to the azine in solution. This explains, in part, the low potency of naloxazone. First, only a portion of naloxazone was converted to its azine and the remaining naloxazone probably competitively inhibited naloxonazine's action. Thus, the irreversible blockade of opiate receptor binding requiring high doses of naloxazone (2 $\mu$M) is reproduced by low (50 nM) doses of naloxonazine.

[$^3$H] Dihydromorphine, [$^3$H] D-ala$^2$-D-leu$^5$-enkephalin, [$^3$H] D-ala$^2$-met$^5$-enkephalinamide, and Formula 963 scintillation fluor were purchased from New England Nuclear Corp. Inc. (Boston, MA), naloxone, naltrexone and oxymorphone from Endo (Garden City, NY) and naloxazone, naltrexazone, and oxymorphazone synthesized as previously described (Pasternak and Hahn, J. Med. Chem 23:674–677, 1980).

The azine derivatives of naloxone, naltrexone and oxymorphone (FIG. 1) were synthesized by reacting a three-fold molar excess of the parent alkaloid in ethanol with naloxazone, naltrexazone and oxymorphazone respectively. The individual reactions which were monitored by thin layer chromatography (TLC) (silica gel, CHCl$_3$:CH$_3$OH:NH$_4$OH,90:10:1) were complete within 3 hr. After evaporation of the solvent in vacuo, products were purified by preparative TLC using the above solvent system. The isolated compounds had an R$_f$identical with the product in the unpurified reaction mixture, suggesting that rearrangement did not occur during purification. The individual alkaloids, naloxonazine, naltrexonazine, and oxymorphonazine, were further characterized ,by their mass, nuclear magnetic resonance (NMR) and infrared (IR) spectra. Mass spectroscopy using chemical ionization detection showed M+1 ions at 651, 679 and 599 respectively. In the NMR spectrum, the downfield shift in the C-5 hydrogen absorption recorded for the hydrazone derivatives (Pasternak and Hahn, J. Med. Chem. 23:674–677, 1980) was also observed for the azine derivatives. The absence of a carbonyl absorption in the IR spectra of the individual compounds further confirmed reaction at C-6 in each of the 14-hydroxydihydromorphinone derivatives. Microanalysis (CHNO-Rockefeller University Microanalytical Laboratory) of each compound also verified the proposed structures. The absence of a free NH$_2$ group was indicated by a negative TNBS test (Pasternak and Hahn, 1980, supra). In contrast to the parent hydrazones which produced a reddish-brown color on standing with TNBS, no color change was seen with any of the azine derivatives.

Binding experiments were performed as previously described using 20 mg/ml of tissue (Pasternak et al, Molec Pharmacol 11:340–351, 1975). In brief, brain membranes were prepared and triplicate samples incubated with [$^3$H] labelled ligands and designated drugs for 30 minutes at 25° C., followed by filtration over Whatman GF/B filters. The filters were then counted in Formular 963 scintillation fluor. Specific binding is defined as the difference in binding in the presence and absence of levallorphan (1 μM). Irreversible inhibition of opiate receptor binding was established by the persistence of binding inhibition despite extensive washes which did reverse any inhibition by the same concentration of naloxone. Each tissue wash included incubation for 10 min. at 37° C., centrifugation and resuspension. Irreversibility experiments included four washes before binding assays were performed, unless otherwise stated.

Figure 1:
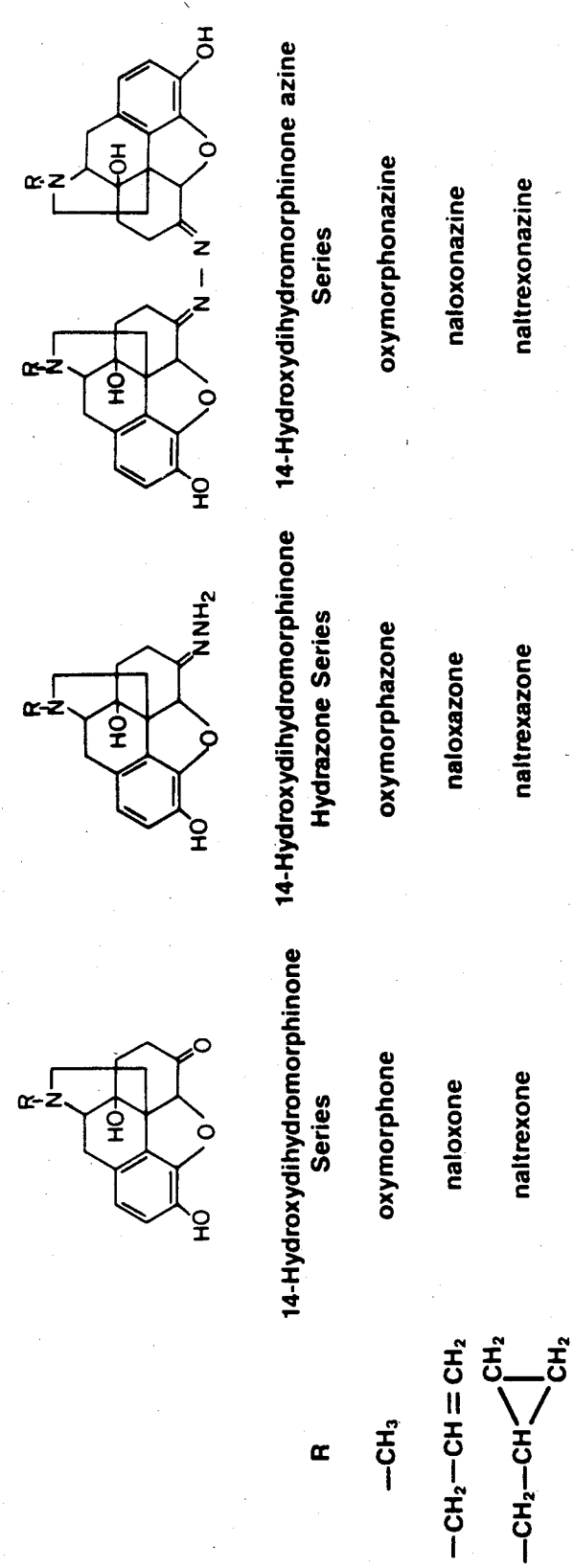
FIG. 1 shows structures of the 14-hydroxydihydromorphinones, their hydrazones and their azines.

The synthesis of monosubstituted hydrazones, such as naloxazone, oxymorphazone and naltrexazone, may be complicated by the formation of azines (FIG. 1). To avoid this problem a large excess of hydrazine was used in the synthesis. Analysis of the compounds, including nuclear magnetic resonance, mass and infra red spectroscopy, thin layer chromatography, CHNO analysis and chemical titration of free -NH$_2$ groups with TNBS (Pasternak and Hahn, J. Med. Chem 23:674–677, 1980) confirmed the formation of a single product and excluded the presence of an azine in each case. However, it is now realized that solutions of the 14-hydroxydihydromorphinone hydrazones rapidly undergo a reaction particularly in acidic aqueous solutions. Isolation and characterization of the product suggested the formation of azines. The direct synthesis of the various 14-hydroxydihydromorphinone azines showed that they were identical to the products formed in the various hydrazone solutions. Having isolated and established the structures of the products as azines, we then determined that they were responsible for the apparent irreversible actions of naloxazone, naltrexazone and oxymorphazone.

PHARMACOLOGICAL COMPARISONS BETWEEN THE 14-HYDROXYDIHYDROMORPHINONES, THEIR HYDRAZONES AND THEIR AZINES.

We first tested the affinity of naloxone and naltrexone, their hydrazones and their azines for opiate receptors (Table 1). Interestingly, the hydrazones and azines displace [$^3$H] dihydromorphine binding less potently than their parent ketones. In both groups, however, the azine is more potent than the hydrazone.

To determine which compounds did irreversibly bind to the receptor membranes were incubated with the various drugs (2 μM) and then the free and reversibly bound drug washed away (Table 2). Special care was taken with the hydrazones to use conditions under which little or no azine formation could be detected. Under these conditions neither naloxazone nor oxymorphazone irreversibly inhibited the binding of either [$^3$H] D-ala$^2$-D-leu$^5$-enkephalin or [$^3$H] dihydromorphine. The small amount of inhibition by naltrexazone reflects the difficulty in totally eliminating azines from its solutions. Making concentrated naloxazone solutions using acetic acid to dissolve the free base as previously reported (Childers and Pasternak, in press), results in a significant amount of azine formation and does irreversibly block the specific binding of both [$^3$H] ligands. However, the far greater potency of the azines suggests that they are the active compound.

TABLE 1

Direct inhibition of [$^3$H]dihydromorphine binding by naloxone, naltrexone and their derivatives.

| Compound | IC$_{50}$ (nM) |
| --- | --- |
| Naloxone | 4.4 ± 0.7 |
| Naloxazone | 16.3 ± 4.9 |
| Naloxonazine | 5.4 ± 1.3 |
| Naltrexone | 0.77 ± 0.05 |
| Naltrexazone | 1.7 ± 0.2 |
| Naltrexonazine | 1.16 ± 20.3 |

Rate brain homogenates were prepared as described and the above drugs at 4 concentrations were incubated with [$^3$H]dihydromorphine (0.8 nM) for 45 min and filtered. IC$_{50}$ values were determined by least square fits of a log-probit curve. The results are the means±s.e.m. of three IC$_{50}$ values determined in separate experiments.

TABLE 2

Irreversible inhibition of receptor binding by naloxone, naltrexone and oxymorphone and their derivations.

| | Change in Binding (Percent) | |
| --- | --- | --- |
| Compound (2 μM) | [$^3$H]D-ala$^2$-D-leu$^5$-enkephal in | [$^3$H]dihydromorphine |
| Naloxone | — | — |
| Naloxazone | +15 ± 5% | +2 ± 11% |
| Naloxazone + acetic acid | −48% ± 11% | −41 ± 13% |
| Naloxonazine | −93% ± 4% | −89 ± 4% |
| Naltrexone | — | — |
| Naltrexazone | −17 ± 19% | −31 ± 26% |
| Naltrexonazine | −97 ± 3% | −88 ± 12% |
| Oxymorphone | — | — |
| Oxymorphazone | 43% ± 24% | +3 ± 21% |
| Oxymorphonazine | −59 ± 3% | −71 ± 4% |

Rat brain membranes were prepared and incubated with the above drugs (2 μM) for 30 min at 25° C. and the tissue was then washed four times as described in the text to remove reversibly bound material. The results represent the means±s.e.m. of three separate experiments utilizing [$^3$H]D-ala$^2$-D-leu $^5$-enkephal in (1 nM) and [$^3$H]dihydromorphine (0.8 nM). With the exception of naloxazone and acetic acid, all drugs were dissolved in absolute ethanol immediately before dilution and addition to tissue. Under these conditions, no azine formation could be detected for naloxazone and oxymoprphazone as demonstrated by thin layer chromatomography. A trace amount of azine was present in the naltrexazone solutions. The naloxazone and acetic acid sample (10 mg/kg) was dissolved in water/acetic acid (1%). After 15 min the solution was added to tissue. Under these conditions a significant portion of the naloxazone had reacted to its azine.

Figure 2:
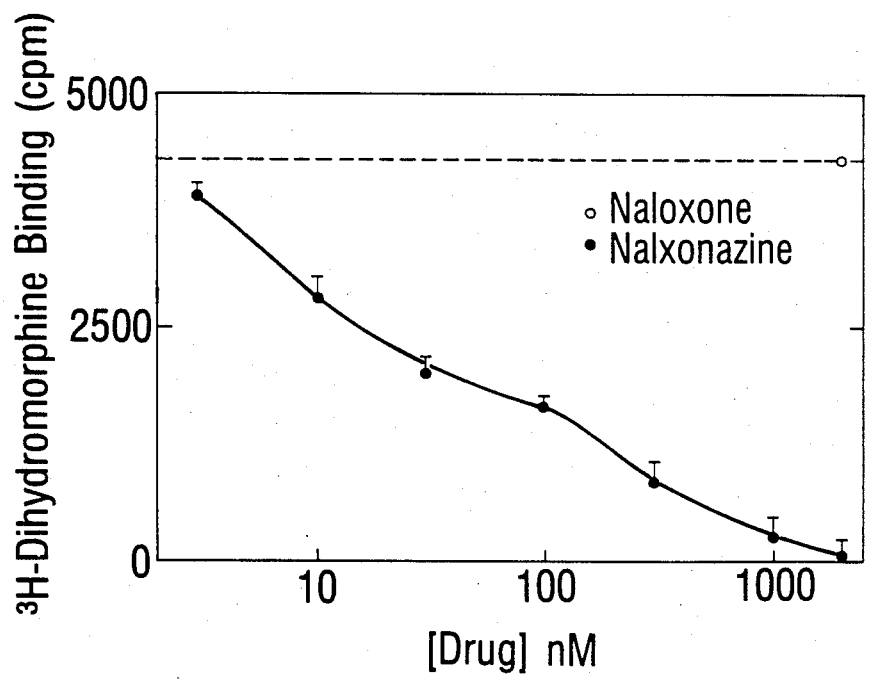
FIG. 2 shows the irreversibility of naloxone and naloxonazine binding in rat brain membranes.

Since naloxonazine at 2 μM eliminated over 90% of [$^3$H] dihydromorphine and [$^3$H] D-ala-$^2$-D-leu$^5$-enkephalin binding, we next examined its irreversible effects at a variety of concentrations (FIG. 2). After incubating membranes with the specified drug, the membranes were extensively washed and a binding assay with [$^3$H] dihydromorphine performed. As expected, naloxone at high concentrations does not inhibit binding irreversibly. Naloxonazine potently inhibits binding in a dose dependent manner. The inhibition curve appears biphasic, suggesting more than one site with differing sensitivities to naloxonazine's irreversible actions. Although it is difficult to accurately determine $IC_{50}$ values without computer analysis, one site appears to be quite sensitive to naloxonazine ($IC_{50}$ about 10–15 nM) while the other requires concentrations approximately 40-fold higher ($IC_{50}$ 400–500 nM).

Previous studies have demonstrated naloxazone's selective inhibition of high affinity, or $mu_1$, binding sites (Pasternak, et al. J. Med. Chem.23:674–677, 1980; Zhang and Pasternak, Life Sci. 29:843–851, 1981; Childers and Pasternak, in press). To determine whether naloxonazine demonstrated the same selectivity described with naloxazone treatment, we incubated tissue with either naloxone or naloxonazine (50 nM), washed the tissue, and examined morphine's displacement of [$^3$H]D-ala$^2$-met$^5$-enkephalinamide binding (FIG. 3). Morphine has the same biphasic displacement in naloxone-treated tissue as previously published (Chang and Cuatrecases, 1978; Zhang and Pasternak, Life Sci. 29:843–851, 1981). The initial morphine displacement represents [$^3$H]D-ala$^2$-met$^5$-enkephalinamide binding to high affinity, or $mu_1$ receptors (Wolozin and Pasternak, in press; Zhang and Pasternak, 1981, supra). Treating the tissue with naloxonazine eliminates this initial displacement, yielding results virtually the same as those using naloxazone. Thus, naloxonazine has the same selectivity but far greater potency than naloxazone.

THE USE OF THE ANTAGONISTS NALOXONAZINE AND NALTREXONAZINE AS APPETITE SUPPRESSANTS

It is known that opiate antagonists such as naloxone and naltrexone effectively suppress eating behavior in rats. In view of the generally good correlation between the pharmacological actions of opiates in animal models and their effects in man, it is therefore believed that these agents will also suppress appetite in man. The major disadvantage of the currently available agents (naloxone and naltrexone) is their short half-life and the need for multiple doses each day. A long-acting agent would have many advantages, especially compliance by the patient and convenience. In addition, whereas naloxone and naltrexone interact with a number of different classes of opiate receptors, naltrexonazine and naloxonazine are far more selective for the mu1 class of opiate binding sites and therefore will have far more selective pharmacological actions in vivo. The major question relevant to this use of the inventive compounds is whether the subpopulation of sites affected by naloxonazine and naltrexonazine are involved in the suppression of appetite. Although direct tests have not been done, tests have been run using naloxazone. As explained above, the actions of naloxazone are believed to result from the conversion of this drug to naloxonazine. It is therefore predicted that all the actions seen with naloxazone will be produced by naloxonazine at far lower doses. The effectiveness of naloxazone was shown, as follows:

Rats were administered either saline or naloxazone was (50 mg/kg intravenously) through cannulae placed in the jugular vein. They were then food deprived for 24 hours but allowed free access to water. Five rats received saline, four received naloxone and three naloxazone. Both naloxone and naloxazone were given at 50 mg/kg intravenously. The animals were then given free access to food for 1 hour and their weight gain noted. Thus, eating was measured 24 hours after the administration of the drugs and after 24 hours of food deprivation.

|  | Amounts eaten in grams: | | |
|---|---|---|---|
|  | Saline | Naloxone | Naloxazone |
|  | 4.1 | 4.1 | 3.3 |
|  | 3.9 | 5.3 | 2.4 |
|  | 4.4 | 4.4 | 3.5 |
|  | 6.1 | 3.7 |  |
|  | 5.4 |  |  |
| Mean ± SEM | 4.78 ± 0.42 | 4.38 ± 0.34 | 3.07 ± 0.34 |

When analyzed by analysis of variance, the above results were significant at the p 0.05 level [$F_{2,9} = 4.56$]

These results indicate that naloxazone has a significant effect as an appetite suppressant. The inability of naloxone to effect feeding behavior does not imply that it has no actions on feeding, but merely emphasizes that its actions are short-lived and clearly illustrates the marked advantages of naloxazone, and thus naloxonazine. In vivo work with naloxonazine has demonstrated that it is 5-fold more active on a mg/kg basis than naloxazone and both drugs have the same actions.

THE USE OF THE AZINES AS SELECTIVE AGENTS IN MODULATING HORMONE RELEASE

The two antagonists naloxonazine and naltrexonazine and the agonist oxymorphonazine have actions lasting far longer than conventional opiates. In addition we have found that the selective interactions of these drugs with the mu1 class of opiate receptors has a selective action on hormone release. An example of this selectivity are the effects of morphine on the release of prolactin and growth hormone. Although morphine releases both hormones it utilizes different classes of opiate receptors. Thus, the selective blockage of the mu1 class can inhibit morphine's action on prlactin release but not growth hormone.

The selective blockade of the mu1 sites in vivo by the prior administration of naloxazone depressed the morphine-induced release of prolactin over 80%. Morphine-induced growth hormone release, on the other hand, was actually increased. The implications of these findings are that different receptors mediate the release of the different hormones by a single drug. Naloxone inhibits morphine's release of both hormones. In comparison, naloxazone has the ability of selectively lowering prolactin release without effecting growth hormone release elicited by morphine and presumably other opiates as well. On the other hand, one might expect the agonist compound oxymorphonazine to selectively elevate prolactin levels without substantially increasing growth hormone concentrations.

The release of many hormones is under the tonic control of opioid systems. The evidence for this effect comes from work demonstrating a lowering of the basal levels of prolactin and growth hormone following the administration of naloxone. Our work also illustrates a significant reduction in the basal levels of the drugs after naloxazone.

THE USE OF THE AZINES IN THE CLASSIFICATION OF OPIOID DRUGS

Recent work has suggested that several classes of opioid receptors exist. One area of immense importance is in the new classification of two types of mu receptors. Up until now, it has been difficult to determine the relative potency of agents for the mu1 and mu2 class of receptor. The affinity of naloxonazine and the other azines for the mu1 class permits the rapid and simple estimation of the potency of agents for the mu2 site and the mu1 by comparison with measures of both types together.

THE USE OF OXYMORPHONAZINE AS AN ANALGESIC AGENT

The advantages of this drug are: (i) long action, (ii) presumed decreased respiratory depressant actions, (iii) presumed decreased inhibition of gastrointestinal motility and thus constipation, (iv) presumed decreased incidence of hypotension. The evidence for many of these decreased side-effects of oxymorphonazine come from evidence suggesting that these other actions reside in receptors other than mu1. Thus the selective interactions of the drug with mu1 sites should result in fewer side-effects.

Evidence of the analgesic effect of oxymorphonazine is shown in the following experiment summary:

| | Oxymorphonazine analgesia in vivo | | | |
|---|---|---|---|---|
| | Analgesia (percent) | | | |
| Time | Oxymorphone Group | | Oxymorphonazine Group | |
| 1 hr. | 100% | n = 14 | 100% | n = 9 |
| 4 hr. | 78% | n = 9 | 100% | n = 5 |
| 10 hr. | 33% | n = 9 | 100% | n = 5 |
| 20 hr. | 0% | n = 14 | 44% | n = 9  p < 0.015 |

Mice were injected with either oxymorphone or oxymorphonazine (both 25 μg in 5 μl of artificial CSF) under Ethrane/oxygen anesthesia and tested for analgesia at the stated time. Analgesia was determined by Tail-Flick Assay. Quantal criteria, the doubling of the baseline latency for each individual animal, was used. At 20 hours, the oxymorphone and oxymorphonazine groups differed from each other at p<0.015 level, as determined by Fisher's Exact Test.

THE USE OF THE ANTAGONISTS NALOXONAZINE AND NALTREXONAZINE AS BLOCKERS OF MORPHINE AND OTHER OPIATES IN MAINTENANCE PROGRAMS FROM OPIOID ABUSERS

The advantage of the agents are their prolonged actions (in the order of days) compared to the duration of currently available drugs (in the order of only a few hours.)

The following test show the effectiveness of this compound as blockers:

| Naloxonazine blockade of morphine analgesia in vivo | |
|---|---|
| | Morphine sulfate $ED_{50}$ value |
| Control group | 3.7 mg/kg s.c. |
| Naloxonazine group | |
| 35 mg/kg | 76.0 mg/kg s.c. |
| 50 mg/kg | 202.7 mg/kg s.c. |

Groups of mice (n=10) were treated with either nothing, or naloxonazine (35 or 50 mg/kg, s.c.) and tested for morphine analgesia 24 hours later. Full dose response curves were performed with at least three separate doses of morphine for each curve. $ED_{50}$ values, that dose of morphine needed to produce analgesia in 50% of animals, was determined by Probit analysis. Analgesia was determined in the Tail-Flick Assay using the quantal measurement of doubling of baseline flick as criteria.

In general, opiate receptor binding/blocking has been shown for a wide range of symmetric and assymetric dihydromorphinone compounds of the type which can be represented as

wherein
HDM is

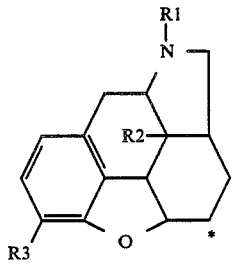

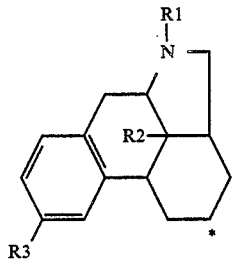

where
* indicates binding carbon
R1 is optionally substituted alkyl, alkylene, cycloalkyl, or cycloalkylene
R2 is OH or H
R3 is OH or OCH3 and
R is N=R4, N-R4,

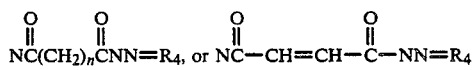

R4 is optionally substituted alkyl, alkylene, cycloalkyl, cycloalkylene, aryl, heterocycloalkyl for example HDM, heterocycloalkylene, or alkenyl, and n is 1-10.

Presently preferred of the dihydromorphinone compounds of the present invention are the 14-hydroxydihydromorphinones especially naloxonazine, naltrexonazine and oxymorphonazine as well as mixed azines. The 3-methoxy derivatives of these compounds are expected to be potent drugs with similar long acting and selective properties since the 3-methoxy derivatives of the ketone derivatives have high oral potency.

Symmetrical compounds (where R is —N=HDM) as exemplified above include
oxymorphonazine (R1=—CH3; R2=OH; R3=OH; HDM=N—N=HDM)
naloxonazine (R1=—CH2—CH=CH2; R2=OH; R3=OH; HDM=N—N=HDM)
naltrexonazine $$(R1 = -CH_2-CH\begin{smallmatrix}CH_2\\ \\ CH_2\end{smallmatrix};$$

R2=OH; R3=OH: HDM=N—N=HDM).

Activity of these compounds was described in detail in the general discussion above.

SYMMETRICAL COMPOUNDS WITH A BRIDGE

The azine linkage itself is not believed to be critical to the activity of the compounds. Thus compounds of the following type should be able to potently inhibit binding:

$$HDM=N-N\underset{H}{C}(CH_2)_n\underset{H}{CN}-N=R4 \text{ or}$$

(non-conjugated bridge)

$$HDM=N-\underset{H}{N}-\overset{O}{\underset{\|}{C}}-CH=CH-\overset{O}{\underset{\|}{C}}-\underset{H}{NN}=R4$$

(conjugated bridge)

In fact activity has been shown in both cases where R1 is $$CH_2-CH\begin{smallmatrix}CH_2\\ \\ CH_2\end{smallmatrix};$$

R2 is OH; R3 is OH; and R4 is HDM; and n=2,4,6. Activity for an extended conjugated bridge is to be expected as well.

ASYMMETRICAL COMPOUNDS HAVE BEEN SHOWN TO BE ACTIVE

The symmetrical nature of the molecule is also not critical. Significant irreversible inhibition of opiate receptor binding under conditions where standard opiates such as morphine show no irreversible inhibition has been shown for the following compounds: of the general formula

NTX=N—R wherein NTX is naltrexone=HDM where $$(R1 = -CH_2-CH\begin{smallmatrix}CH_2\\ \\ CH_2\end{smallmatrix};$$

and R2=R3=OH)

NTX=N—N—⟨phenyl⟩
(note: not an azine)

NTX=N—N—⟨phenyl⟩—NO2
(note: not an azine)

NTX=N—N—CH3
(note: not an azine)

$$NTX=N-N=C\begin{smallmatrix}CH_3\\ \\ CH_3\end{smallmatrix}$$

(note: an azine)

ASYMMETRIC COMPOUNDS WITH MIXED AGONIST/ANTAGONIST COMPONENTS ARE ALSO ACTIVE

In vivo texts have been run on mixed agonist/antagonist compounds, viz naltrexone-oxymorphonazine. These asymmetric compounds appear to irreversibly bind the opiate receptors and act as antagonists.

Tests were run in binding assays with analogs of morphine and the endogenous opioid enkephalin compounds comparing these asymmetric compounds with symmetric naltrexonazine to show irreversible blocking of receptor sites as follows:

| | Irreversible Inhibition of $^3$H—Opioid Binding by Naltrexone-Oxymorphonazine | |
|---|---|---|
| Treatment | $^3$H—DADL Binding (cpm) | $^3$H—DHM Binding (cpm) |
| Nothing (control) | 1800 ± 53 | 3447 ± 273 |
| Naltrexonazine | 653 ± 85 (−65%) | 1183 ± 128 (−66%) |
| Naltrexone-oxymorphonazine | 1205 ± 157 (−33%) | 1487 ± 120 (−57%) |

Rat brain homogenates were incubated with either nothing or naltrexonazine or naltrexone-oxymorphonazine at 100 nM for 30 min at 25° C. and then washed twice. Each wash consisted of centrifugation, incubation at 37° for 10 min and centrifugation again. Under these conditions, reversible ligands such as naloxone, naltrexone and oxymorphone are all effectively removed. Bindig was then performed with either $^3$H-D-ala$^2$-D-leu$^5$-enkephalin (DADL) or $^3$H-dihydromorphine (DHM) both at 1 nM. Specific binding was determined as that displaceable by levallorphan at 1000 nM. All values represent the means of triplicate samples±S.E.M.

Action as an antagonist for the asymmetric compound as compared with the corresponding symmetric compound was shown as follows:

| In vivo actions of Naltrexone-oxymorphonazine | | | |
|---|---|---|---|
| | Tailflick Latencies (sec) | | |
| Drug | Prior | After 20 min | After 40 min |
| naltrexone (10 mg/kg) n = 10 | 2.63 ± 0.27 | 2.37 ± 0.31 | 2.59 ± 0.35 |
| naltrexone-oxymorphona- zine (10 mg/kg) n = 10 | 2.44 ± 0.32 | 2.20 ± 0.35 | 2.29 ± 0.31 |
| naltrexonazine (10 mg/kg) n = 9 | 2.50 ± 0.34 | 2.50 ± 0.36 | 2.74 ± 0.49 |

Groups of mice were injected subcutaneously with the stated drug and latencies in the tailflick test determined and compared to those obtained prior to testing. Using the doubling of baseline latencies, none of the animals receiving the mixed azine (naltrexone-oxymorphonazine) were analgesic. This compares with an analgesic rate of 100% of animals receiving oxymorphone HCl in other control experiments.

It will be understood that the specification and examples are illustrative but not limitative of the present invention and that other embodiments within the spirit and scope of the invention will suggest themselves to those skilled in the art.

What is claimed is:

1. Dihydromorphinone compound of the general formula

wherein

HDM is 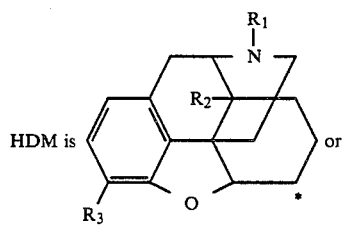 or 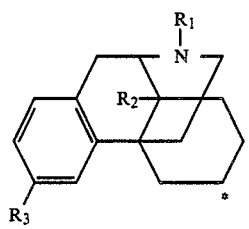

R1 is alkyl with 1 to 10 carbon atoms or alkenyl of 2 to 10 carbon atoms,
R2 is OH or H,
R3 is OH,

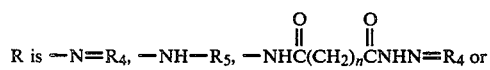

-continued $$-NHCCH=CHCNHN=R_4,$$ (with O, O above the C's)

R4 is HDM, alkenylidene with 2 to 10 carbon atoms, or cycloalkenylidene of up to 6 carbon atoms,
R5 is phenyl, alkyl of 1 to 4 carbon atoms, alkenyl with 2 to 10 carbon atoms, cycloalkyl of up to 6 carbon atoms, or cycloalkenyl of up to 6 carbon atoms and
n is 1-10.

2. Method of controlling appetite comprising selectively and/or irreversibly blocking the mu1 opiate receptors by administering an effective amount of a dihydromorphinone compound of the formula

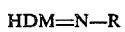

wherein

HDM is 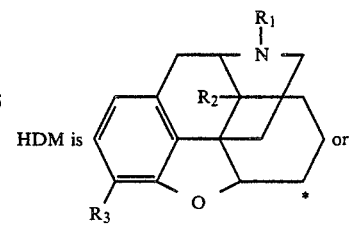 or 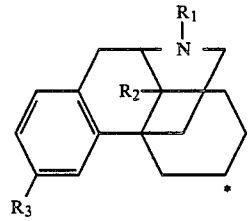

wherein
* indicates binding carbon
R1 is alkyl with 1 to 10 carbon atoms or alkenyl of 2 to 10 carbon atoms,
R2 is OH or H
R3 is OH or OCH3 and

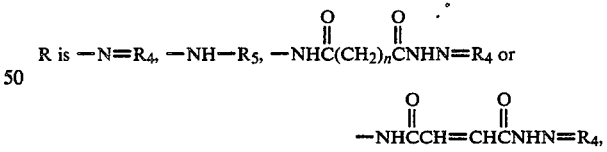

R4 is HDM, alkenylidene with 2 to 10 carbon atoms, or cycloalkenylidene of up to 6 carbon atoms,
R5 is phenyl, alkyl of 1 to 4 carbon atoms, alkenyl with 2 to 10 carbon atoms, cycloalkyl of up to 6 carbon atoms, or cycloalkenyl of up to 6 carbon atoms and
n is 1-10.

3. Method of reducing opiate dependency in an addict comprising administering an effective amount of the compound of claim 1.

* * * * *

UNITED STATES PATENT AND TRADEMARK OFFICE
CERTIFICATE OF CORRECTION

PATENT NO. : 4,608,376

DATED : August 26, 1986

INVENTOR(S) : Gavril W. Pasternak

It is certified that error appears in the above-identified patent and that said Letters Patent is hereby corrected as shown below:

Title page:

After "Assignee" please change "Carolyn McGinnis, New York, N.Y." to -- Sloan-Kettering Institute for Cancer Research, New York, N.Y. --.

Signed and Sealed this

Eighteenth Day of October, 1988

Attest:

DONALD J. QUIGG

*Attesting Officer*  *Commissioner of Patents and Trademarks*